United States Patent
Yen et al.

(10) Patent No.: US 10,758,764 B2
(45) Date of Patent: Sep. 1, 2020

(54) FLOOR MAT STRUCTURE AND FLOOR MAT ASSEMBLY

(71) Applicants: Shih-Hsiung Yen, Taipei (TW); Chia-Hung Ou, Taipei (TW); Ta-Hsiang Huang, Taipei (TW); June-Peng Lai, Taipei (TW); Fu-Hsuan Tseng, Taipei (TW); Ching-Tai Chang, Taipei (TW)

(72) Inventors: Shih-Hsiung Yen, Taipei (TW); Chia-Hung Ou, Taipei (TW); Ta-Hsiang Huang, Taipei (TW); June-Peng Lai, Taipei (TW); Fu-Hsuan Tseng, Taipei (TW); Ching-Tai Chang, Taipei (TW)

(73) Assignee: COMPAL ELECTRONICS, INC., Taipei (TW)

( * ) Notice: Subject to any disclaimer, the term of this patent is extended or adjusted under 35 U.S.C. 154(b) by 0 days.

(21) Appl. No.: 16/195,862

(22) Filed: Nov. 20, 2018

(65) Prior Publication Data
US 2019/0151697 A1 May 23, 2019

Related U.S. Application Data

(60) Provisional application No. 62/588,906, filed on Nov. 20, 2017.

(51) Int. Cl.
*A63B 6/00* (2006.01)
*F21V 33/00* (2006.01)
*A61B 5/11* (2006.01)
*H05B 47/10* (2020.01)
*H05B 47/105* (2020.01)

(52) U.S. Cl.
CPC .......... *A63B 6/00* (2013.01); *A61B 5/11* (2013.01); *A61B 5/1126* (2013.01);
(Continued)

(58) Field of Classification Search
CPC .. A63B 6/00; A63B 6/02; A63B 6/025; A63B 21/4037; A63B 69/3661;
(Continued)

(56) References Cited

U.S. PATENT DOCUMENTS 5,848,830 A * 12/1998 Castle ................ A47G 27/0243
362/84
6,417,778 B2 * 7/2002 Blum ...................... A47L 23/22
340/815.4
(Continued)

FOREIGN PATENT DOCUMENTS

| CN | 106647431 | 5/2017 |
|----|-----------|--------|
| TW | I544952 | 8/2016 |

*Primary Examiner* — Jennifer Robertson
*Assistant Examiner* — Thao N Do
(74) *Attorney, Agent, or Firm* — JCIPRNET

(57) ABSTRACT

A floor mat structure includes an upper cover, a plurality of light bars, a lower cover and at least one sensing element. The upper cover includes a main body and a plurality of indicator blocks. The main body has an upper surface and a lower surface opposite to each other. The indicator blocks are separated from one another and are disposed on the lower surface. The light bars are disposed on the upper cover and are embedded in the upper surface. The lower cover assembled to the upper cover includes a base and a plurality of bumps. The base has a configuration surface facing the lower surface. The bumps are separated from one another and are disposed on the configuration surface, wherein orthographic projections of the indicator blocks on the configuration surface does not overlap the bumps. The sensing element is disposed on the lower cover and are located at at least one bump. When the sensing element senses pressure from the upper cover, the light bars illuminate. Also, a floor mat assembly is provided.

25 Claims, 13 Drawing Sheets

(52) U.S. Cl.
CPC ............ *F21V 33/008* (2013.01); *H05B 47/10* (2020.01); *H05B 47/105* (2020.01); *A61B 2560/0443* (2013.01); *A61B 2562/0247* (2013.01); *A61B 2562/0252* (2013.01); *A61B 2562/046* (2013.01); *F21V 33/00* (2013.01)

(58) Field of Classification Search
CPC ............ A63B 69/3691; A63B 71/0054; A63B 2209/23; A63B 2209/14; A63B 22/00; A63B 17/00; A63B 23/00; A63B 2208/00; A63B 2208/02; A63B 2230/62; A63B 2230/00; A63B 2207/00; A63B 2220/10; F21V 33/008; H05B 47/10; A61B 5/1126; E04F 13/074; E04F 13/072; E04F 15/024; A63F 13/218; A63F 13/214
USPC .......................................................... 482/4
See application file for complete search history.

(56) References Cited

U.S. PATENT DOCUMENTS

| | | | |
|---|---|---|---|
| 6,844,058 B2 * | 1/2005 | Blum | A47L 23/22 15/104.002 |
| 7,670,022 B2 * | 3/2010 | Kessler | A47L 23/266 362/153 |
| 7,905,645 B2 * | 3/2011 | Batti | A47G 27/0243 362/234 |
| 8,444,294 B1 * | 5/2013 | Hawkins | A47G 27/0212 362/100 |
| 9,561,396 B2 * | 2/2017 | Lazarchik | |
| 9,722,332 B1 * | 8/2017 | Lin | A63H 33/08 |
| 2003/0177723 A1 * | 9/2003 | Jakob-Bamberg | E04F 15/024 52/263 |
| 2003/0232698 A1 * | 12/2003 | Couvillion, Jr. | G09B 9/00 482/4 |
| 2010/0234183 A1 * | 9/2010 | Mar | A63B 21/4037 482/8 |
| 2011/0072581 A1 * | 3/2011 | Villa | A63B 21/4037 5/420 |
| 2012/0058861 A1 * | 3/2012 | Satut | A63B 6/00 482/8 |
| 2014/0342118 A1 * | 11/2014 | Connaughton | B32B 3/266 428/139 |
| 2016/0375296 A1 * | 12/2016 | Downey | E04F 15/225 52/506.01 |
| 2018/0117380 A1 * | 5/2018 | Lin | A63B 6/02 |
| 2018/0369041 A1 * | 12/2018 | Sheth | A61B 5/6892 |
| 2019/0070478 A1 * | 3/2019 | McCall | A63B 69/3661 |

* cited by examiner

FLOOR MAT STRUCTURE AND FLOOR MAT ASSEMBLY

CROSS-REFERENCE TO RELATED APPLICATION

This application claims the priority benefit of U.S. provisional application Ser. No. 62/588,906, filed on Nov. 20, 2017. The entirety of the above-mentioned patent application is hereby incorporated by reference herein and made a part of this specification.

BACKGROUND

Technical Field

The disclosure relates to a floor mat structure and a floor mat assembly, and particularly to a floor mat structure having a sensing function and a floor mat assembly.

Description of Related Art

General floor mats are mostly made of elastic materials, and a larger cushion may be formed through splicing the edges of the floor mats to provide buffer force to protect users so that the users may play and exercise on the cushion. However, the known floor mat only has a function of providing buffer force and cannot satisfy users' needs for multi-functions of a product; thus, the known floor mat is not economic effective.

SUMMARY

The disclosure provides a floor mat structure and a floor mat assembly having multi-functions including the functions of protection and pressure sensing.

A floor mat structure of the disclosure includes an upper cover, a plurality of light bars, a lower cover, and at least one sensing element. The upper cover includes a main body and a plurality of indicator blocks. The main body has an upper surface and a lower surface that are opposite to each other. The indicator blocks are separated from one another and are disposed on the lower surface of the main body. The light bars are disposed on the upper cover and are embedded in the upper surface of the main body. The lower cover assembled to the upper cover includes a base and a plurality of bumps. The base has a configuration surface facing the lower surface. The bumps are separated from one another and are disposed on the configuration surface of the base, wherein orthographic projections of the indicator blocks on the configuration surface do not overlap the bumps. The sensing element is disposed on the lower cover and is located at the bump, wherein when the sensing element senses pressure from the upper cover, the light bars illuminate.

In an embodiment of the disclosure, the abovementioned upper cover further includes a plurality of protruding portions, which are located at the lower surface of the main body. Orthographic projections of the protruding portions on the configuration surface completely overlaps the bumps.

In an embodiment of the disclosure, the abovementioned main body of the upper cover, indicator blocks and protruding portions are integrally formed.

In an embodiment of the disclosure, the abovementioned main body of the upper cover has a plurality of first locking portions, and the base of the lower cover has a plurality of second locking portions. The first locking portions lock up the second locking portions respectively, so as to make the upper cover assembled to the lower cover.

In an embodiment of the disclosure, the abovementioned main body of the upper cover has a plurality of grooves, and the grooves are located at the upper surface, and the light bars are located in the grooves respectively.

In an embodiment of the disclosure, the abovementioned light bars illuminate blue light, red light green light or combinations thereof.

In an embodiment of the disclosure, the abovementioned light bars are arranged as a triangle, and the light bars are in series, in parallel or in serial parallel with one another.

In an embodiment of the disclosure, the abovementioned floor mat structure further includes an illuminating pattern, disposed on the upper cover and embedded in the upper surface of the main body, wherein the light bars surround the illuminating pattern.

In an embodiment of the disclosure, the abovementioned illuminating pattern includes numbers, words, symbols or combinations thereof.

In an embodiment of the disclosure, the abovementioned bumps are arranged in an array on the configuration surface of the base, and the orthographic projections of the indicator blocks on the configuration surface are closed to the bumps.

In an embodiment of the disclosure, the shape of the bumps is cylindrical.

In an embodiment of the disclosure, the abovementioned sensing element is a sensing film having a plurality of sensing points and the sensing points are located on the pumps respectively.

In an embodiment of the disclosure, the abovementioned floor mat structure further includes a plurality of buffers disposed on the lower cover and located at the bumps, wherein the buffers surround the sensing element to support the upper cover.

In an embodiment of the disclosure, the abovementioned floor mat structure further includes at least one connector disposed on the lower cover and located at at least one side of the base, wherein the light bars and sensing elements are electrically connected to the connector respectively.

In an embodiment of the disclosure, the abovementioned floor mat structure further includes a plurality of first electric wires and at least one second electric wire. The first electric wires are connected to the light bars and connector. The second electric wire is connected to the sensing element and connector.

In an embodiment of the disclosure, the abovementioned main body of the upper cover has a plurality of outlets penetrating through the upper surface and the lower surface. One ends of the first electric wires are extended through the outlets to connect to the light bars, and the other ends of the first electric wires are extended to the configuration surface of the base and are connected to the connector.

In an embodiment of the disclosure, the abovementioned floor mat structure further includes a wire spring having a first end and a second end, wherein the first end is fixed on the base of the lower cover and the first electric wire extends through the second end.

In an embodiment of the disclosure, the abovementioned base of the lower cover has a bottom surface with respect to the configuration surface and at least one storage groove. The storage groove is disposed on the bottom surface and the connector is stored in the storage groove.

In an embodiment of the disclosure, the abovementioned floor mat structure further includes at least an encapsulation adhesive tape. The connector is fixed in the storage groove with the encapsulation adhesive tape.

In an embodiment of the disclosure, the abovementioned floor mat structure further includes a circuit board passing through parts of the bumps and disposed on the base of the lower cover. The light bars and sensing element are electrically connected to the circuit board respectively.

In an embodiment of the disclosure, the abovementioned floor mat structure further includes a protection cover passing through parts of the bumps and covering the circuit board.

In an embodiment of the disclosure, the abovementioned floor mat structure further includes an antenna module disposed on the lower cover and located at the base. The antenna module is electrically connected to the circuit board.

In an embodiment of the disclosure, the abovementioned floor mat structure further includes a plurality of fasteners. Each fastener includes a sleeve and a screw. The sleeve passes through the lower cover and upper cover and the screw is threaded through the sleeve to make the lower cover fixed to the upper cover through the fasteners.

The floor mat assembly of the disclosure includes a plurality of the abovementioned floor mat structures and at least one connector. The floor mat structure includes at least one first floor mat structure and at least one second floor mat structure. The second floor mat structure further includes a first circuit board; and light bars and sensing elements of the second floor mat structure and light bars and sensing elements of the first floor mat structure are electrically connected to the first circuit board. The first floor mat structure is spliced together with the second floor mat structure through the fasteners.

In an embodiment of the disclosure, the abovementioned floor mat structure further includes a third floor mat structure spliced with the first and second floor mat structures through fasteners. The third floor mat structure further includes a second circuit board and an antenna module electrically connected to the second circuit board. The light bars and sensing elements of the third floor mat structure are electrically connected to the second circuit board, and the second circuit board is electrically connected to the first circuit board.

Based on the above, in the design of the floor mat structure of the disclosure, the sensing element is disposed on the bumps of the lower cover. When users put pressure on the floor mat structure to make the sensing element sense the pressure from the upper cover, the light bars disposed on the upper cover may illuminate, so as to form an interaction relationship between the users and the floor mat structure. Moreover, the bumps of the lower cover can be used as a support to withstand the pressure imposed on the floor mat structure thereby reducing the probability of damage to the floor mat structure. Besides, since the orthographic projections of the indicator blocks of the upper cover on the configuration surface of the lower cover does not overlap the bumps, the orthographic projections may be used to instruct operators the following wire management works to avoid contacting the bumps. In brief, the floor mat structure of the disclosure has multi-functions including the functions of protection and pressure sensing.

In order to make the features and advantages of the disclosure mentioned above more understandable, embodiments will be described in detail below with reference to the accompanying drawings.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1A:
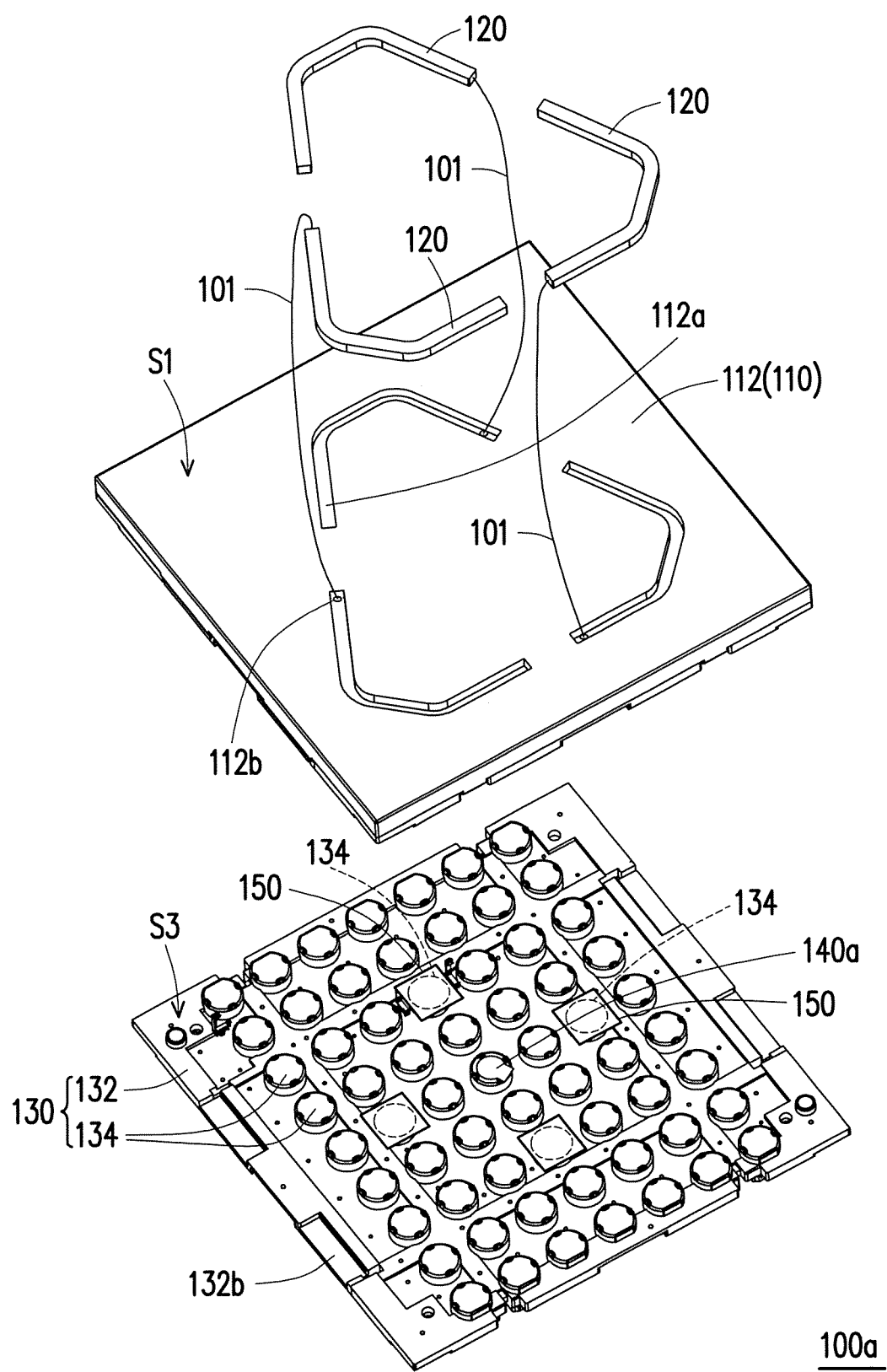
FIG. 1A is a partial exploded schematic view of a perspective of a floor mat structure of an embodiment of the disclosure.
Figure 1B:
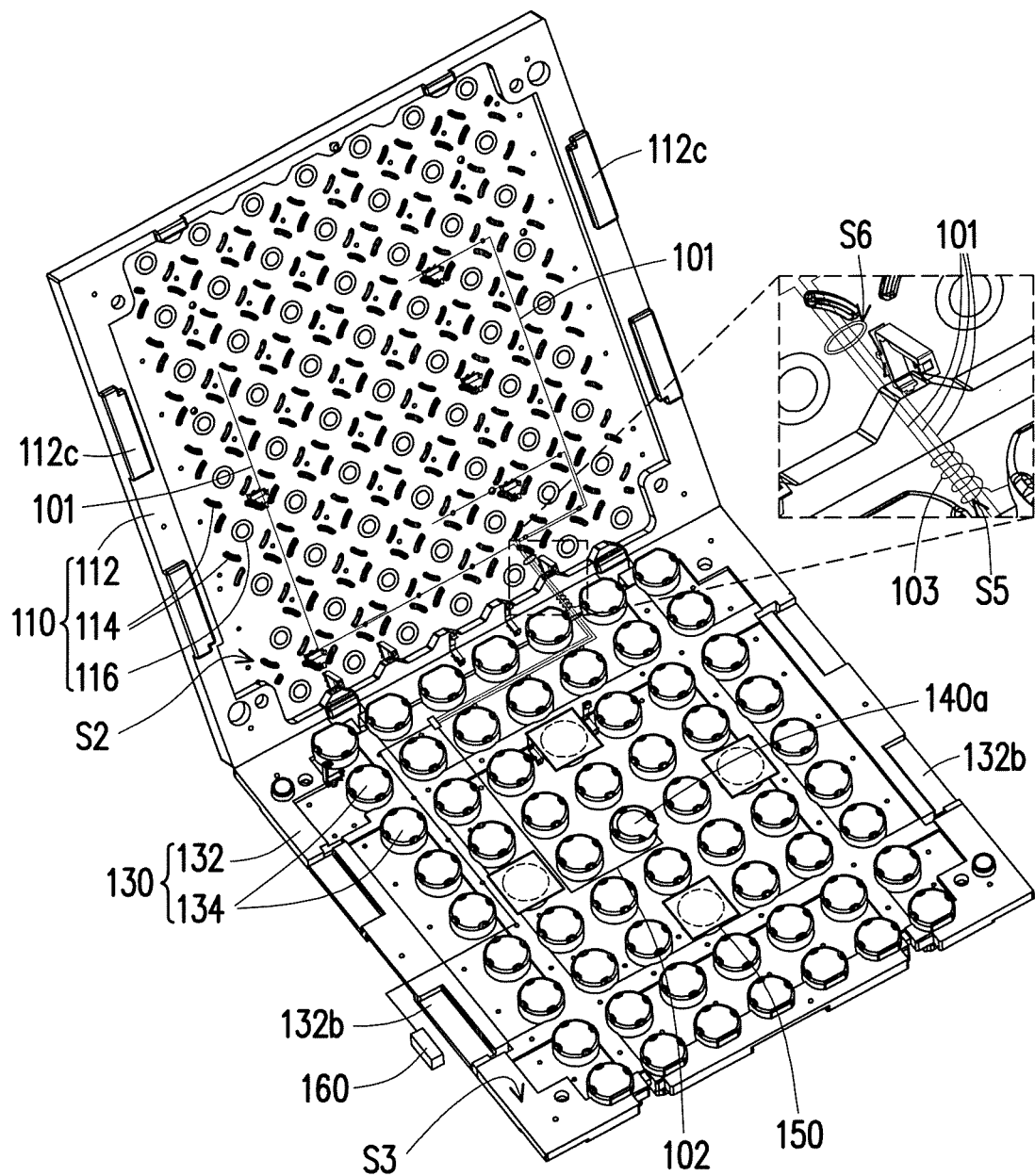
FIG. 1B is a schematic view of the floor mat structure of FIG. 1A with its upper cover opened with respect to its lower cover.
Figure 1C:
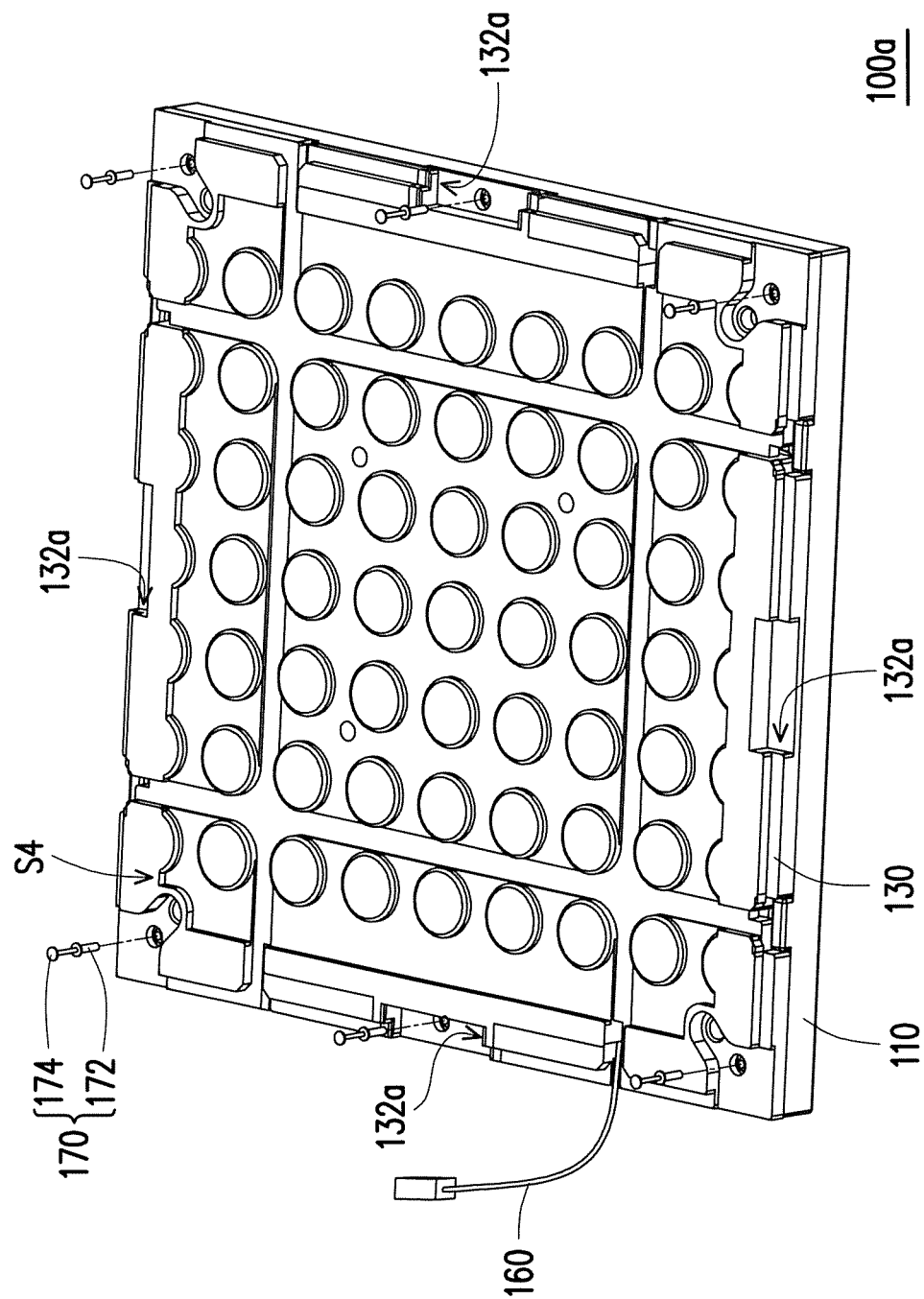
FIG. 1C is a partial exploded schematic view of another perspective of the floor mat structure of FIG. 1A.
Figure 1D:
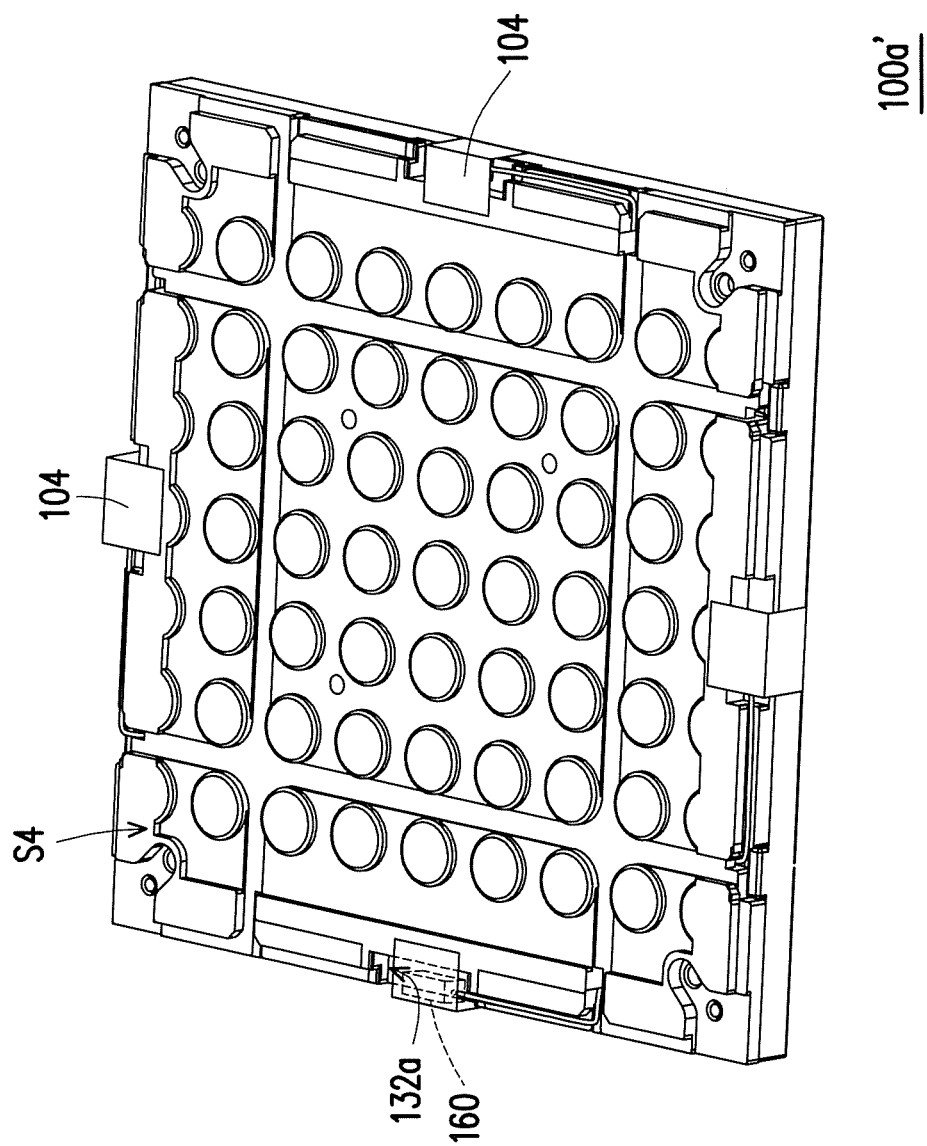
FIG. 1D is a schematic view of a floor mat structure of another embodiment of the disclosure.

FIG. 1A is a partial exploded schematic view of a perspective of a floor mat structure of an embodiment of the disclosure. FIG. 1B is a schematic view of the floor mat structure of FIG. 1A with its upper cover opened with respect to its lower cover. FIG. 1C is a partial exploded schematic view of another perspective of the floor mat structure of FIG. 1A. FIG. 1D is a schematic view of a floor mat structure of another embodiment of the disclosure.

Please refer to FIG. 1A, FIG. 1B and FIG. 1C simultaneously. A floor mat structure 100a of the present embodiment includes an upper cover 110, a plurality of light bars 120 (three light bars are shown schematically in FIG. 1A), a lower cover 130 and at least one sensing element 140a (one sensing element is shown schematically in FIG. 1A). The upper cover 110 includes a main body 112 and a plurality of indicator blocks 114. The main body 112 has an upper surface S1 and a lower surface S2 that are opposite to each other. The indicator blocks 114 are separated from one another and are disposed on the lower surface S2 of the main body 112. The light bars 120 are disposed on the upper cover 110 and are embedded in the upper surface S1 of the main body 112. The lower cover 130 is assembled to the upper cover 110, wherein the lower cover 130 includes a base 132 and a plurality of bumps 134. The base 132 has a configuration surface S3 facing the lower surface S2, and the bumps 134 are separated from one another and are disposed on the configuration surface S3 of the base 132. Particularly, when the upper cover 110 and the lower cover 130 are accurately assembled, orthographic projections of the indicator blocks 114 on the configuration surface S3 does not overlap the bumps 134. The sensing element 140a is disposed on the lower cover 130 and located at the bumps 134. When the sensing element 140a senses the pressure from the upper cover 110, the light bars 120 illuminates.

In details, the main body 112 of the upper cover 110 has a certain hardness and can withstand the pressure given by the users. The indicator blocks 114 are disposed on the lower surface S2 of the main body 112, that is, the indicator blocks 114 protrude from the lower surface S2. At this time, the area surrounded by indicator blocks 114 can be regarded as a concave surface; thus, the concave surface and the bumps 134 of the lower cover 130 form a concave convex corresponding structure. In the present embodiment, the purpose of disposing the indicator blocks 114 is to indicate to operators so that the operators can avoid the wires from contacting the bumps 134 of the lower cover 130 in the following wire management works. The upper cover 110 of the present embodiment further includes a plurality of protruding portions 116 located at the lower surface S2 of the main body 112. When the upper cover 110 and the lower cover 130 are accurately assembled, the orthographic projections of the protruding portions 116 on the configuration surface S3 completely overlap the bumps 134. Preferably, the shape of the bumps 134 is embodied, for instance, as cylindrical, and can withstand the pressure uniformly. The main body 112 of the upper cover 110, the indicator blocks 114 and the protruding portions 116 are integrally formed through, for instance, a method of press molding. Since the orthographic projections of the protruding portions 116 on the configuration surface S3 completely overlap the bumps 134, the sensing element 140a disposed on the bumps 134 can maintain a good sensing sensitivity after being used for a long-time.

The main body 112 of the upper cover 110 of the present embodiment further has a plurality of grooves 112a, wherein the grooves 112a are located at the upper surface S1, and the light bars 120 are respectively located in the grooves 112a. That is, the grooves 112a can accommodate the light bars 120, wherein the shape and size of the grooves 112a are substantially the same as the shape and size of the light bars 120. Preferably, the light bars 120 can be fixed in the grooves 112a by applying glue (not shown) to the inside of the grooves 112a or on the light bars 120. After the assembly, the light bars 120 can be leveled with the upper surface S1 of the main body 112 or slightly lower than the upper surface S1 of the main body 112, and the disclosure is not limited thereto.

In an embodiment, the floor mat structure 100a can electrically connect to the sensing element 140a by using an external circuit (not shown), and then when the sensing element 140a senses pressures from the upper cover 110, the light bars 120 illuminate. Herein, the light bars 120 and the sensing element 140a can be electrically connected to the external circuits in a wireless manner. The light bars 120, for instance, consist of a plurality of light emitting diodes (not shown) through a transparent encapsulating materials (not shown), and can illuminate blue light, red light, green light and combinations thereof, and is not limited thereto. As shown in FIG. 1A, the light bars 120 of the present disclosure are embodied as a type of triangle, wherein the light bars 120 can be connected in series, in parallel or in serial parallel with one another, and is not limited thereto. For example, the light bars 120 may be electrically connected to the external circuit after being connected in series, or may be electrically connected to the external circuit after being connected in parallel with each other.

In the present embodiment, in order to easily allow the floor mat structure 100a to be electrically connected to the external circuits (not shown), the floor mat 100a may further include at least one connector 160, wherein the connector 160 is disposed on the lower cover 130 and is located at one side of a base 132, and the light bars 120 and the sensing element 140a are electrically connected to the connector 160. More specifically, the floor mat structure 100a further includes a plurality of first electric wires 101 and at least one second wire 102. The first electric wires 101 are electrically connected to the light bars 120 and the connector 160, and the second electric wire 102 is electrically connected to the sensing element 140a and the connector 160. The main body 112 of the upper cover 110 of the present embodiment has a plurality of outlets 112b, wherein the outlets 112b penetrate through the upper surface S1 and the lower surface S2, and one ends of the first electric wires 101 extend through the outlets 112b to connect to the light bars 120 as shown in FIG. 1A. On another front, the other ends of the first electric wires 101 extend to the configuration surface S3 of the base 132 and are connected to the connector 160 as shown in FIG. 1B. In short, the light bars 120 of the floor mat structure 100a and the sensing element 140a can be electrically connected to the external circuits (not shown) through the methods wireless transmission or wired transmission.

It is worth noting that although FIG. 1B and FIG. 1C only schematically show one connector 160, the disclosure does not limit the number of the connectors 160, and the number of the connectors 160 may increase according to the actual requirement. For instance, a floor mat structure 100a may, for instance, have two connectors 160, three connectors 160 or four connectors 160 disposed on four sides of the base 132, and is still within the scope of protection of the disclosure.

Please refer to FIG. 1B to FIG. 1C simultaneously again. For aesthetic reasons, the base 132 of the lower cover 130 of the present embodiment has a bottom surface S4 with respect to the configuration surface S3 and at least one storage groove 132a (four storage grooves are shown schematically in FIG. 1B). The storage groove 132a is disposed on the bottom surface S4 and the connector 160 is stored in the storage groove 132a. Moreover, in another embodiment, please refer to FIG. 1D, the floor mat structure 100a' of the present embodiment may further include an encapsulation adhesive tape 104, wherein the connector 160 in the storage groove 132a can be fixed in the storage groove 132a with the encapsulation adhesive tape 104.

Besides, in order to make the first electric wire 101 connected to the connector 160 more smoothly and to avoid the configuration of the electric wires from affecting the aesthetics of the whole floor mat structure 100a after assembling the upper cover 110 and the lower cover 130, the floor mat structure 100a of the present embodiment further includes a wire spring 103. The wire spring 103 has a first end S5 and a second end S6, wherein the first end S5 is fixed on the base 132 of the lower cover 130, and the first electric wires 101 are extended through the second end S6. The second end S6 is, for instance, a hollow circle, allowing the first electric wires 101 to extend through the second end S6, further making the first electric wires 101 fixed between the upper cover 110 and the lower cover 130 without moving, and may avoid the first electric wires 101 from wearing out due to right-angle bending.

Please refer to FIG. 1A, FIG. 1B and FIG. 1C simultaneously again, the base 132 of the lower cover 130 has a certain hardness and can withstand the pressure given by the users. The bumps 134 of the lower cover 130 are arranged in an array on the configuration surface S3 of the base 132, and when the upper cover 110 and the lower cover 130 are accurately assembled, the orthographic projections of the indicator blocks 114 on the configuration surface S3 are closed to the bumps 134. That is, the orthographic projections of the indicator blocks 114 on the configuration surface S3 are located around the bumps 134, reminding and instructing operators the locations of the bumps 134 through the design of the indicator blocks 114. The bumps 134 of the lower cover 130 can be used as a support to withstand the pressure imposed on the floor mat structure 100a, thereby reducing the probability of damage to the floor mat structure 100a. The sensing element 140a is disposed on the bumps 134 through, for instance, a release film (not shown), wherein the sensing element 140a is used to sense the pressure applied by the users, which means the sensing element 140a is a pressure sensing element. When the number of the sensing elements 140 is plural, the arrangement of the sensing elements 140a may be decided depending on the requirements (entertainment, sport or medical purpose), and the disclosure is not limited thereto.

In order to prevent the weight of the upper cover 110 from affecting the sensitivity of the sensing element 140a, the floor mat structure 100a of the present embodiment further includes a plurality of buffers 150, wherein the buffers 150 are disposed on the lower cover 130 and are located at the bumps 134. Preferably, the buffers 150 surround the sensing element 140a to support the upper cover 110, and the thickness of the buffers 150 is, for instance, greater than the thickness of the sensing element 140a. Therefore, the sensing element 150 can be used to support the weight of the upper cover 110, allowing the upper cover 110 to contact the sensing element 140 after being imposed a certain pressure, so as to assure that the sensing element 140a receives the correct motion messages.

Moreover, please refer to FIG. 1B again, the main body 112 of the upper cover 110 of the present embodiment has a plurality of first locking portions 112c, and the base 132 of the lower cover 130 has a plurality of second locking portions 132b. The first locking portions 112c lock up the second portions 132b respectively to assemble the upper cover 110 to the lower cover 130. Preferably, one of the first locking portions 112c and the second locking portions 132b is embodied as a card slot, and the other one of the first locking portions 112c and the second locking portions 132b is embodied as a card block. Herein, the first locking portions 112c are embodied as a card block and the second locking portions 132b are embodied as a card slot. It should be noted that the first locking portions 112c respectively locking up the second locking portions 132b can limit the relative location of the upper cover 110 to lower cover 130. In order to further fix the upper cover 110 and lower cover 130, please refer to FIG. 1C, the floor mat structure 100a of the present embodiment further includes a plurality of fasteners 170, wherein the fasteners 170 include a sleeve 172 and a screw 174. The sleeve 172 passes through the lower cover 130 and the upper cover 110, and the screw 174 is threaded through the sleeve 172, so as to make the lower cover 130 fixed on the upper cover 110 through the fasteners 170. Herein, the fasteners 170 are, for example, expansion screws, but the disclosure is not limited thereto.

In short, in the present embodiment, the sensing element 140a of the floor mat structure 100a is disposed on the bumps 134 of the lower cover 130. When the user applies pressure on the floor mat structure 100a to make the sensing element 140a sense the pressure from the upper cover 110, the light bars 120 disposed on the upper cover 110 can illuminate to form an interaction relationship between the floor mat structure 100a and the user. Moreover, the bumps 134 of the lower cover 130 can be used as a support to withstand the pressure imposed on the floor mat structure 100a, thereby reducing the probability of damage to the floor mat structure 100a. In addition, since the orthographic projections of the indicator blocks 114 of the upper cover 110 on the configuration surface S3 of the lower cover 130 does not overlap the bumps 134, the orthographic projections can be used to indicate operators in the following wire management works to avoid contacting the bumps 134. Briefly, the floor mat structure 100a of the present embodiment has multi-functions including the functions of protection and pressure sensing.

It should be explained here that the following embodiments use the same reference numerals of the aforementioned embodiments and parts of the description thereof, wherein the same reference numerals are used to represent the same or similar elements, and the description of the same technical contents are omitted. Regarding the description of the omitted parts, please refer to the aforementioned embodiments. The same technical contents will not be repeated in the following embodiment.

Figure 2:
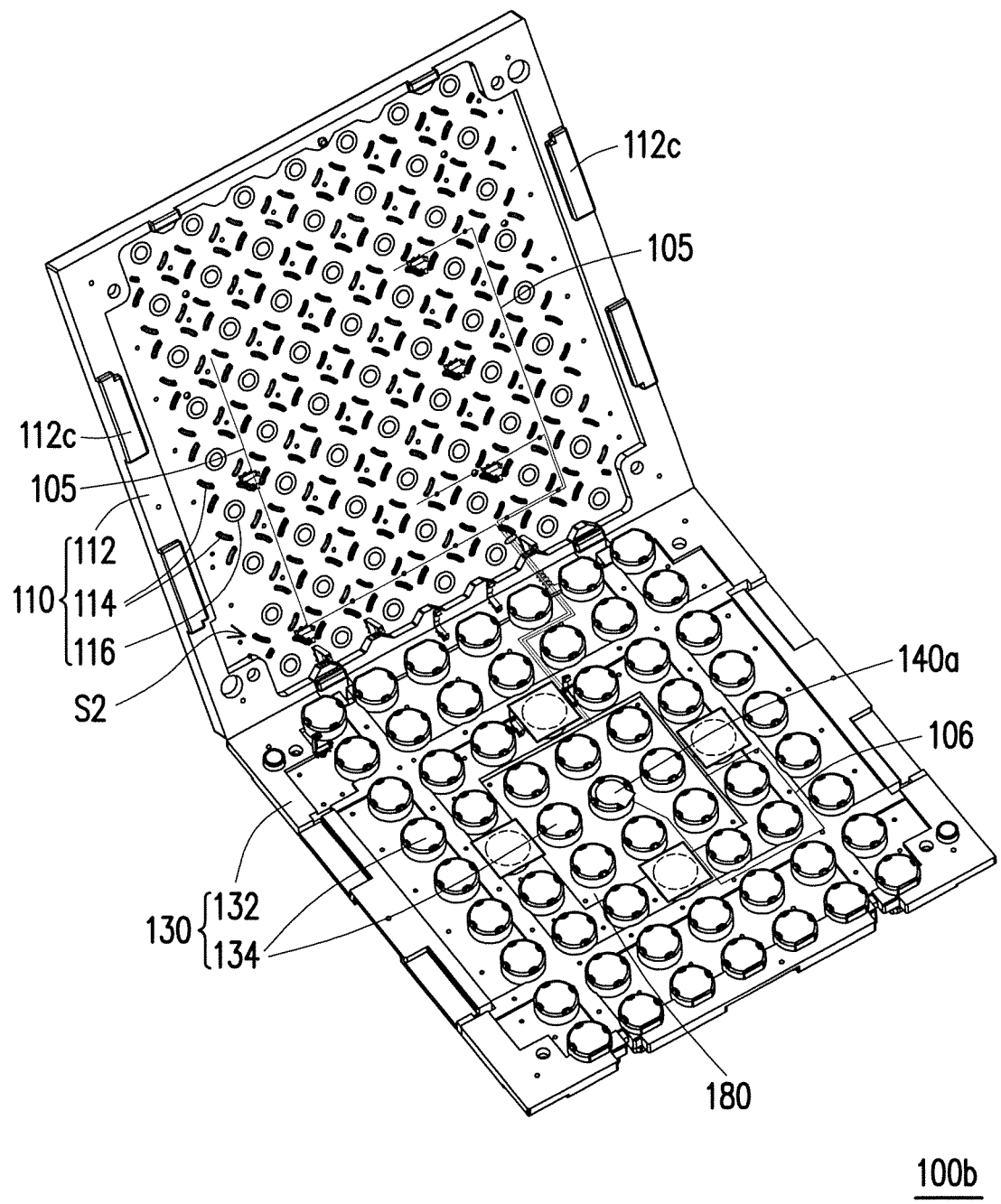
FIG. 2 is a schematic view of a floor mat structure of another embodiment of the disclosure with its upper cover opened with respect to its lower cover.

FIG. 2 is a schematic view of a floor mat structure of another embodiment of the disclosure with its upper cover opened with respect to its lower cover. Please refer to FIG. 1B and FIG. 2 simultaneously, the floor mat structure 100b of the present embodiment is similar to the floor mat structure 100a of FIG. 1B, and the difference between the two is that the floor mat structure 100b of the present embodiment further includes a circuit board 180. The circuit board 180 passes through a portion of bumps 134 and is disposed on the base 132 of the lower cover 130. The light bars 120 and the sensing element 140a are respectively electrically connected to the circuit board 180. Furthermore, the light bars 120 can be electrically connected to the circuit board 180 through a third electric wire 105, and the sensing element 140a is electrically connected to the circuit board 180 through a fourth electric wire 106. Through the signal transmission of the circuit board 180, when the sensing element 140a senses the pressure of the upper cover 110, the light bars 120 can illuminate.

Figure 3:
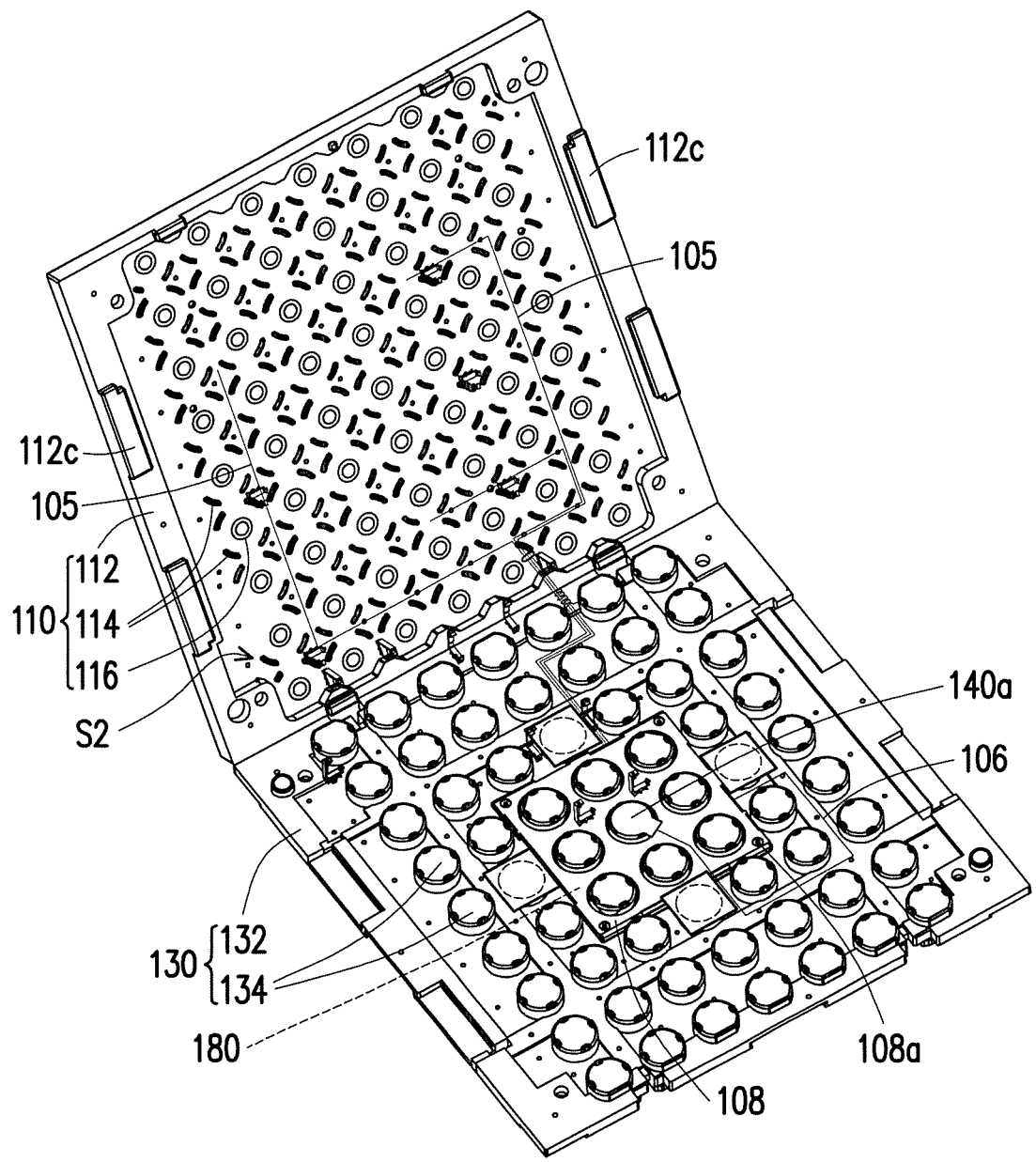
FIG. 3 is a schematic view of a floor mat structure of another embodiment of the disclosure with its upper cover opened with respect to its lower cover.

FIG. 3 is a schematic view of a floor mat structure of another embodiment of the disclosure with its upper cover opened with respect to its lower cover. Please refer to FIG. 2 and FIG. 3 simultaneously, the floor mat structure 100c of the present embodiment is similar to the floor mat structure 100b of FIG. 2, and the difference between the two is that the floor mat structure 100c of the embodiment further includes a protective cover 108. The protective cover 108 passes through a portion of the bumps 134 and covers a circuit board 180. Herein, the protective cover 108 may be fixed to the circuit board 180 by the screw 108a to further protect the circuit board 180.

Figure 4:
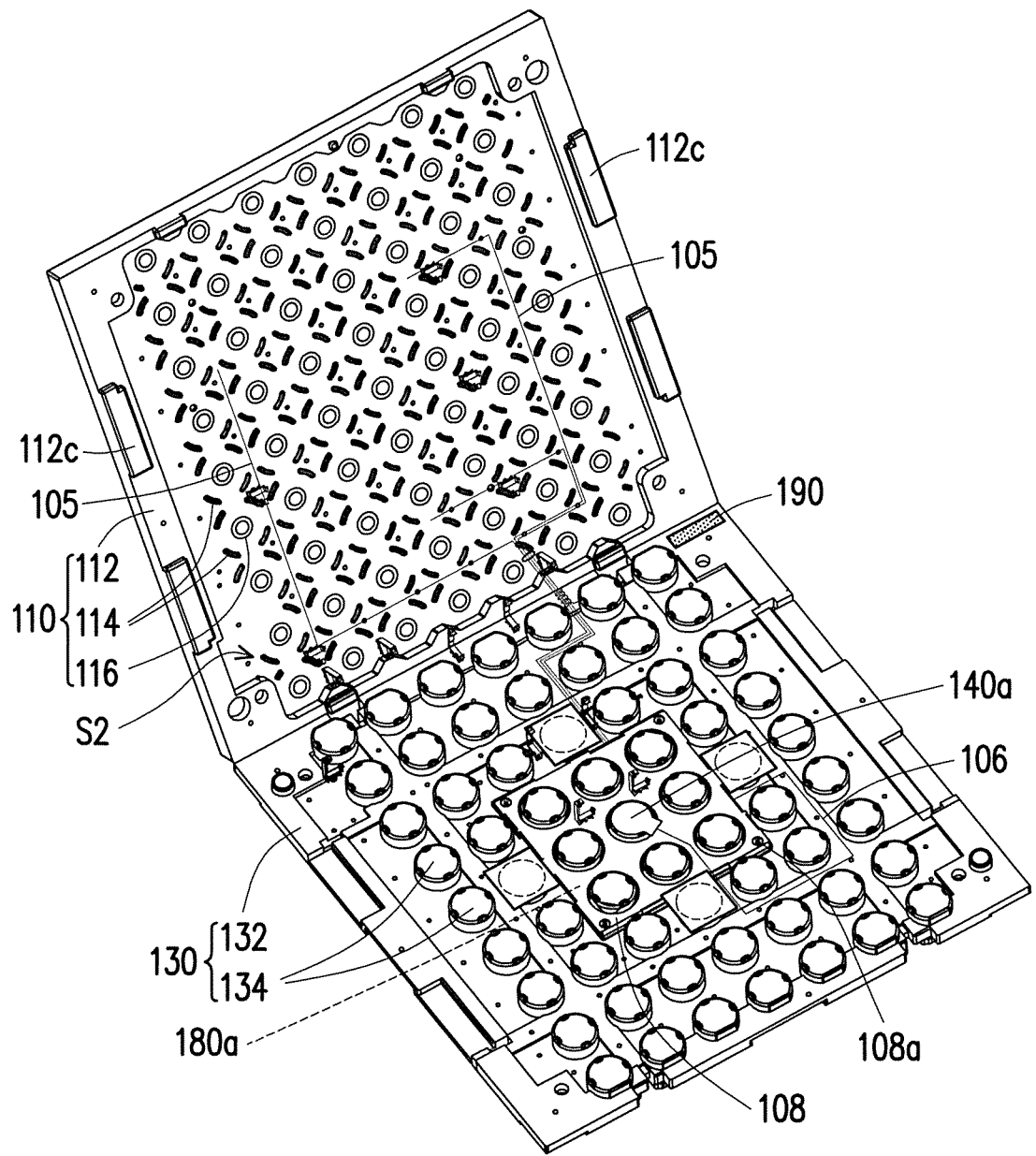
FIG. 4 is a schematic view of a floor mat structure of another embodiment of the disclosure with its upper cover opened with respect to its lower cover.

FIG. 4 is a schematic view of a floor mat structure of another embodiment of the disclosure with its upper cover opened with respect to its lower cover. Please refer to FIG. 3 and FIG. 4 simultaneously, the floor mat structure 100d of the present embodiment is similar to the floor mat structure 100c of FIG. 3, and the difference between the two is that the floor mat structure 100d further includes an antenna module 190. The antenna module 190 is disposed on the lower cover 130 and is located at the base 132, and the antenna module 190 is electrically connected to a circuit board 180a. Herein, the antenna module 190 can be electrically connected to the circuit board 180a by means of wireless transmission, so as to make the circuit board 180a connected to the external system through the antenna module 190.

Figure 5:
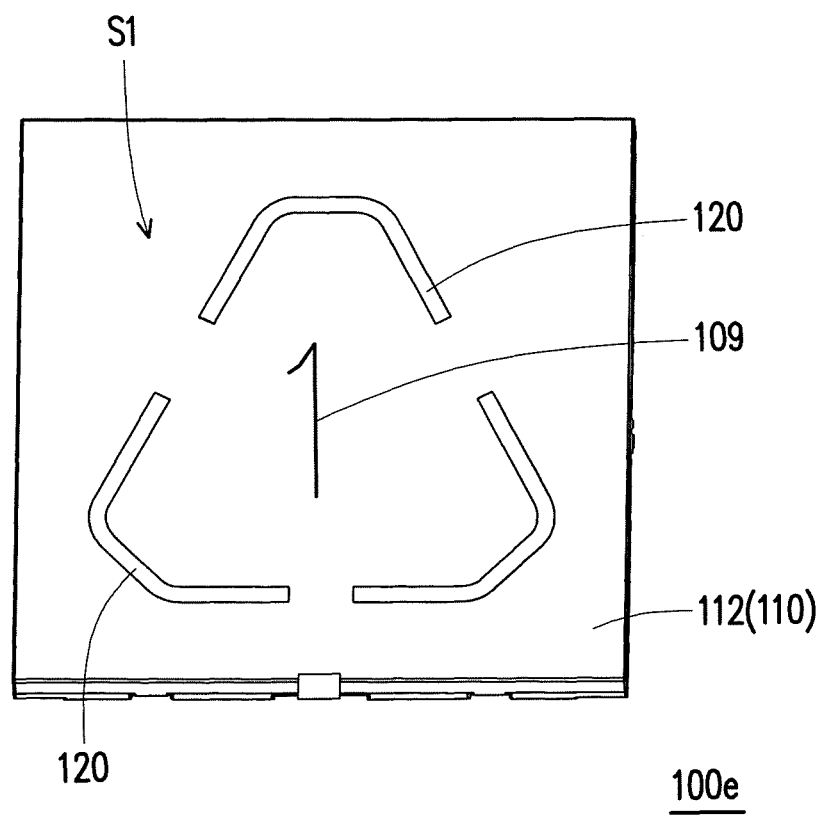
FIG. 5 is a schematic top view of a floor mat structure of another embodiment of the disclosure.

FIG. 5 is a schematic top view of a floor mat structure of another embodiment of the disclosure. Please refer to FIG. 1A and FIG. 5 simultaneously, the floor mat structure 100e of the present embodiment is similar to the floor mat structure 100a of FIG. 1A, and the differences of the two is that the floor mat structure 100e of the present embodiment further includes an illuminating pattern 109. The illuminating pattern 109 is disposed on the upper cover 110 and is embedded in the upper surface S1 of the main body 112, wherein the light bars 120 surround the illuminating pattern 109, and the illuminating patter 109 may include numbers, words, symbols or combinations thereof. Herein, as shown in FIG. 5, the illuminating patter 109 is embodied as numbers, but is not limited thereto.

Figure 6:
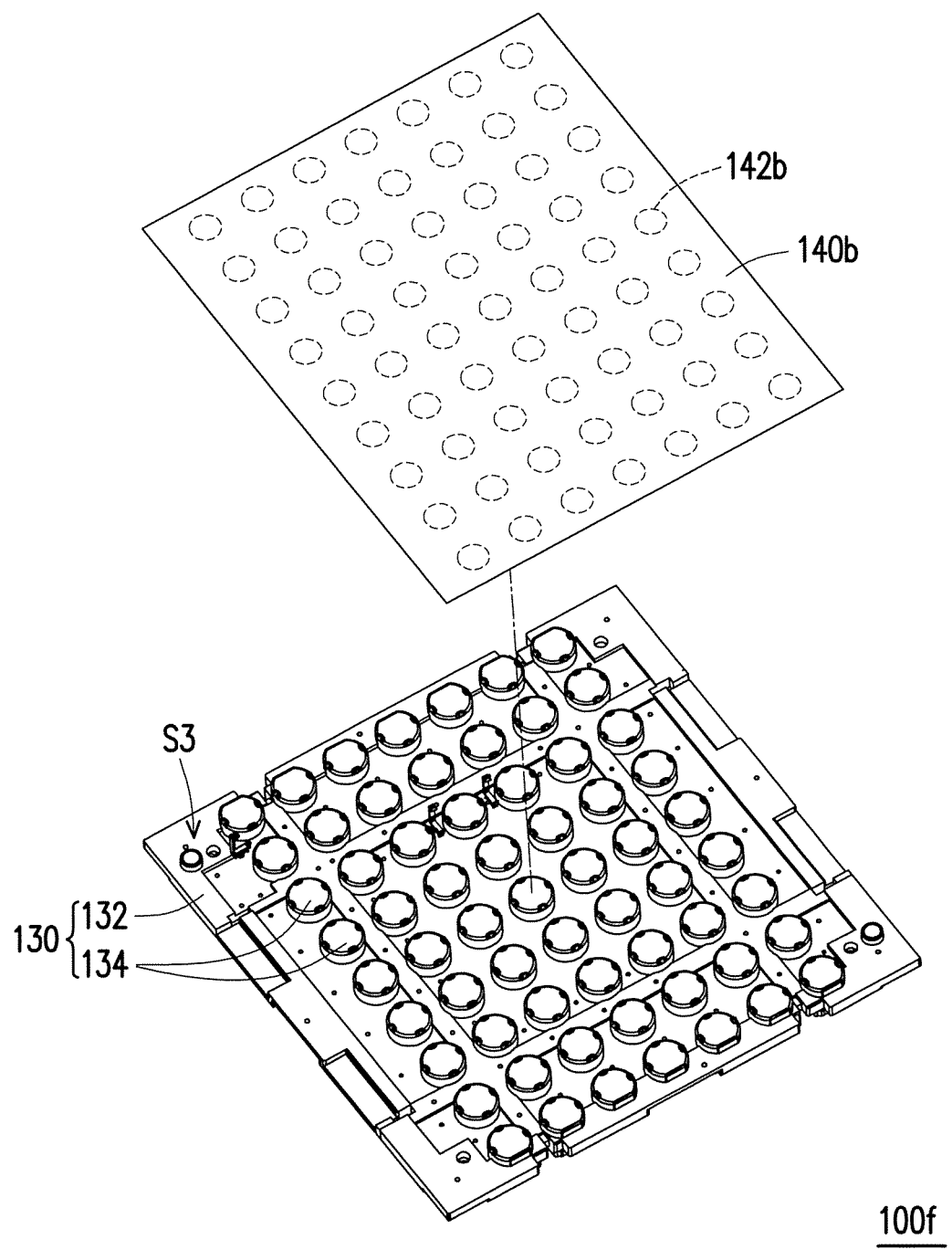
FIG. 6 is an exploded schematic view of a sensing element and a lower cover of a floor mat structure of another embodiment of the disclosure.

FIG. 6 is an exploded schematic view of a sensing element and a lower cover of a floor mat structure of another embodiment of the disclosure. To clearly show the view, parts of components of a floor mat structure 100f of FIG. 6 are omitted. Please refer to FIG. 1A and FIG. 6 simultaneously, the floor mar structure 100f of the present embodiment is similar to the floor mat structure of 100a of FIG. 1A, and the difference of the two is that the sensing element 140b of the present embodiment is embodied as a sensing film, wherein the sensing element 140b has a plurality of sensing points 142b, and the sensing points 142b are located at the pumps 134 respectively. The sensing element 140b of the floor mat structure 100f has the sensing points 142b and is therefore suitable for the application of medical gait analysis.

Figure 7A:
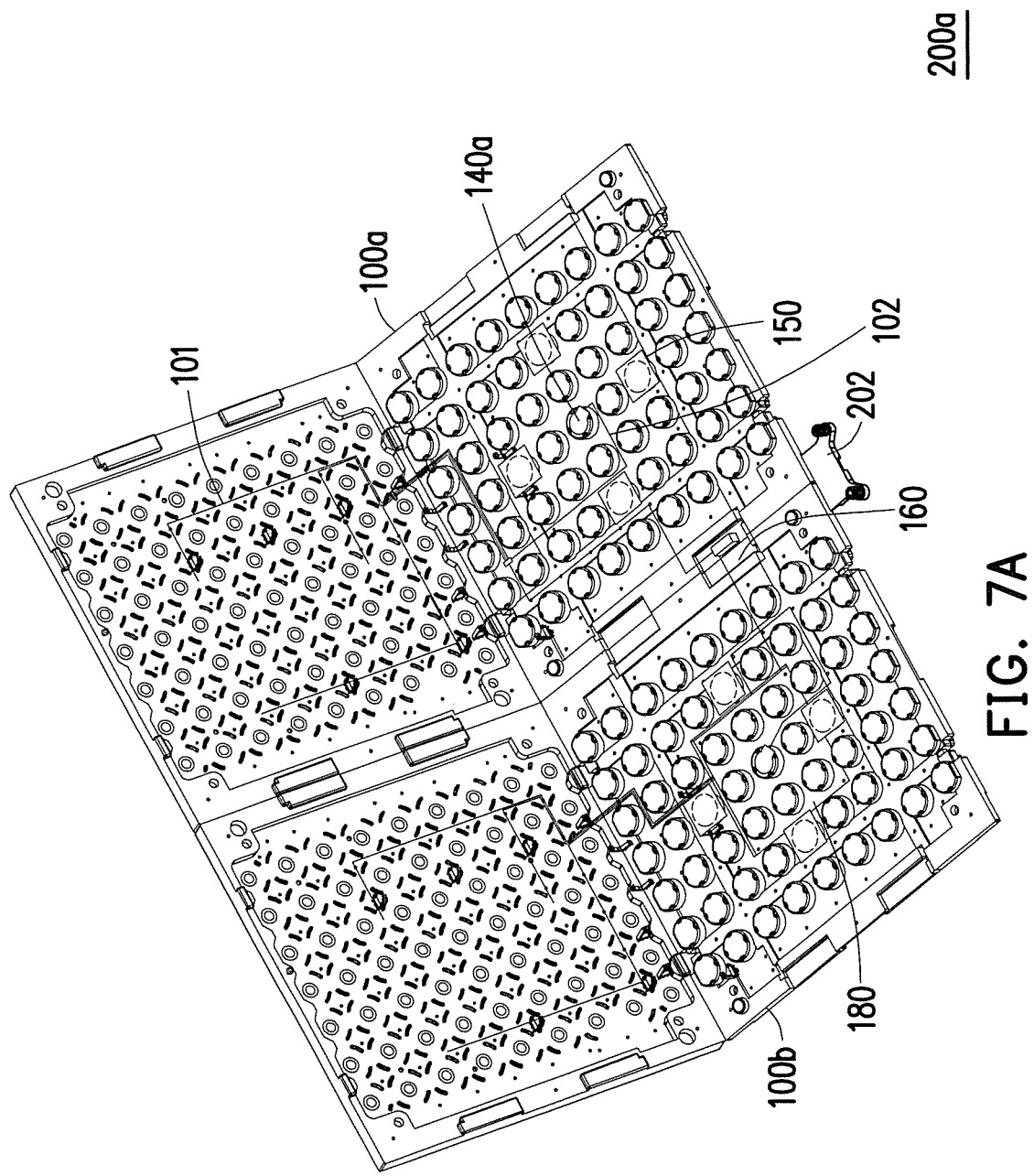
FIG. 7A is a schematic view of a floor mat assembly of an embodiment of the disclosure.

FIG. 7A is a schematic view of a floor mat assembly of an embodiment of the disclosure. Please refer to FIG. 7A, a floor mat assembly 200a of the present embodiment includes the floor mat structure 100a (please refer to FIG. 1B), 100b (please refer to FIG. 2) and a connecting component 202, wherein the floor mat structure 100a and 100b are spliced together through the connecting component 202. Herein, the floor mat structure 100b includes the circuit board 180 (i.e. a first circuit board), and the light bars 120 and the sensing element 140a of the floor mat structure 100b and the light bars 120 and the sensing element 140a of the floor mat structure 100a are electrically connected to the circuit board 180. Herein, the light bars 120 and the sensing element 140a of the floor mat structure 100a can be electrically connected to the circuit board 180 through the connector 160. Moreover, the connecting component 202 of the present embodiment can correspond to the holes on the corner between the floor mat structure 100a and floor mat structure 100b, so as to respectively lock up the floor mat structure 100a and floor mat structure 100b. The floor mat structure 100a can be spliced together with the floor mat structure 100b through the connector component 202 to prevent deformation of the floor mat structure 100a and floor mat structure 100b. In addition, the connecting component 202 facilitates alignment and structural integrity during subsequent packaging or use, and may further prevent relative sliding between the floor mat structure 100a and the floor mat structure 100b during transport or during use.

Figure 7B:
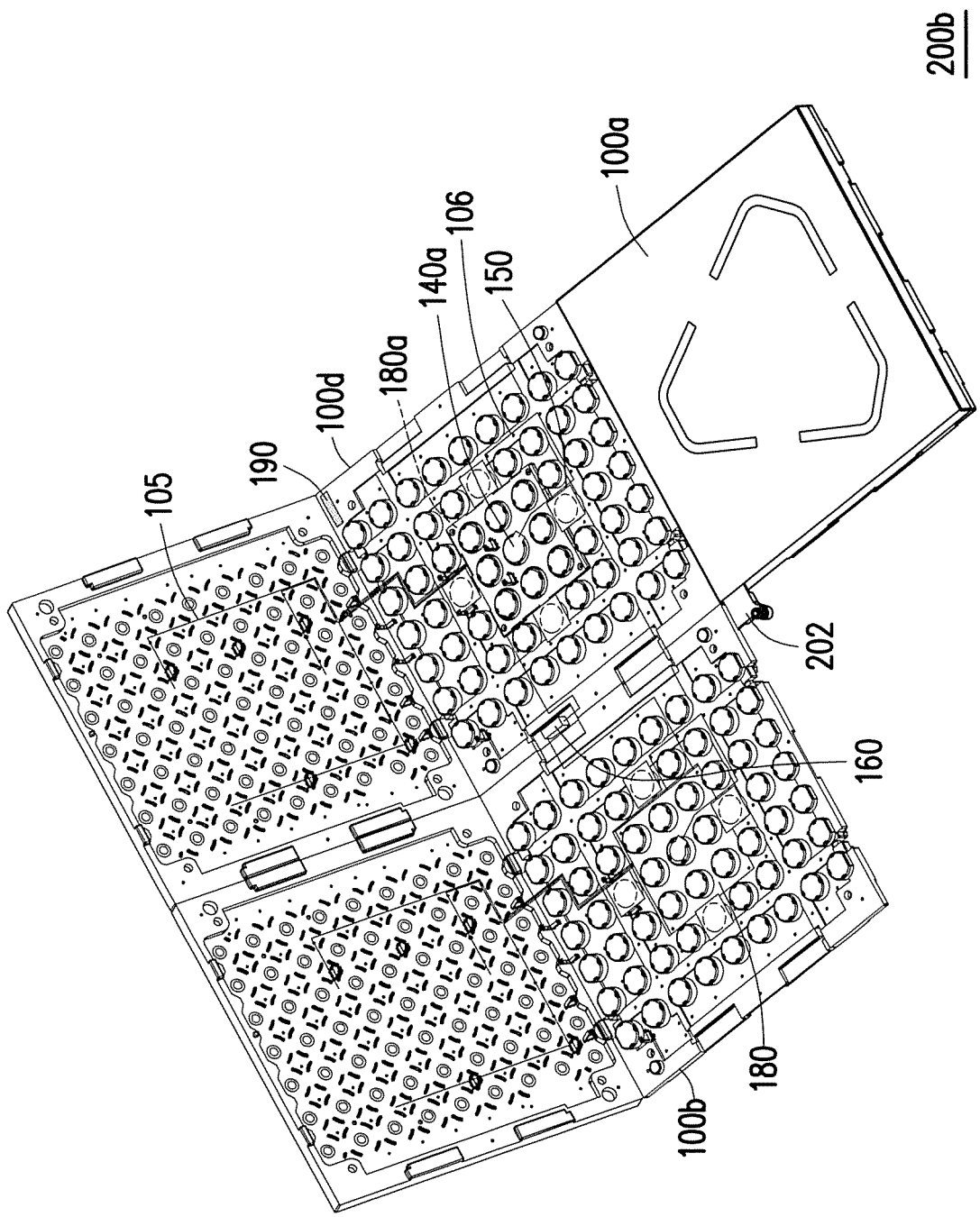
FIG. 7B is a schematic view of a floor mat assembly of an embodiment of the disclosure.

FIG. 7B is a schematic view of a floor mat assembly of an embodiment of the disclosure. Please refer to FIG. 7A and FIG. 7B simultaneously, a floor mat assembly 200b of the present embodiment further includes the floor mat structure 100d (please refer to FIG. 4), wherein a floor mat structure 100d is spliced together with the floor mat structure 100a and the floor mat structure 100b through the connecting component 202. Herein, the floor mat structure 100d includes the circuit board 180a (i.e. a second circuit board) and the antenna module 190 electrically connected to the circuit board 180a. The light bars 120 and the sensing element 140a of the floor mat structure 100b is electrically connected to the circuit board 180, and the circuit board 180 is electrically connected to the circuit board 180a.

Figure 8A:
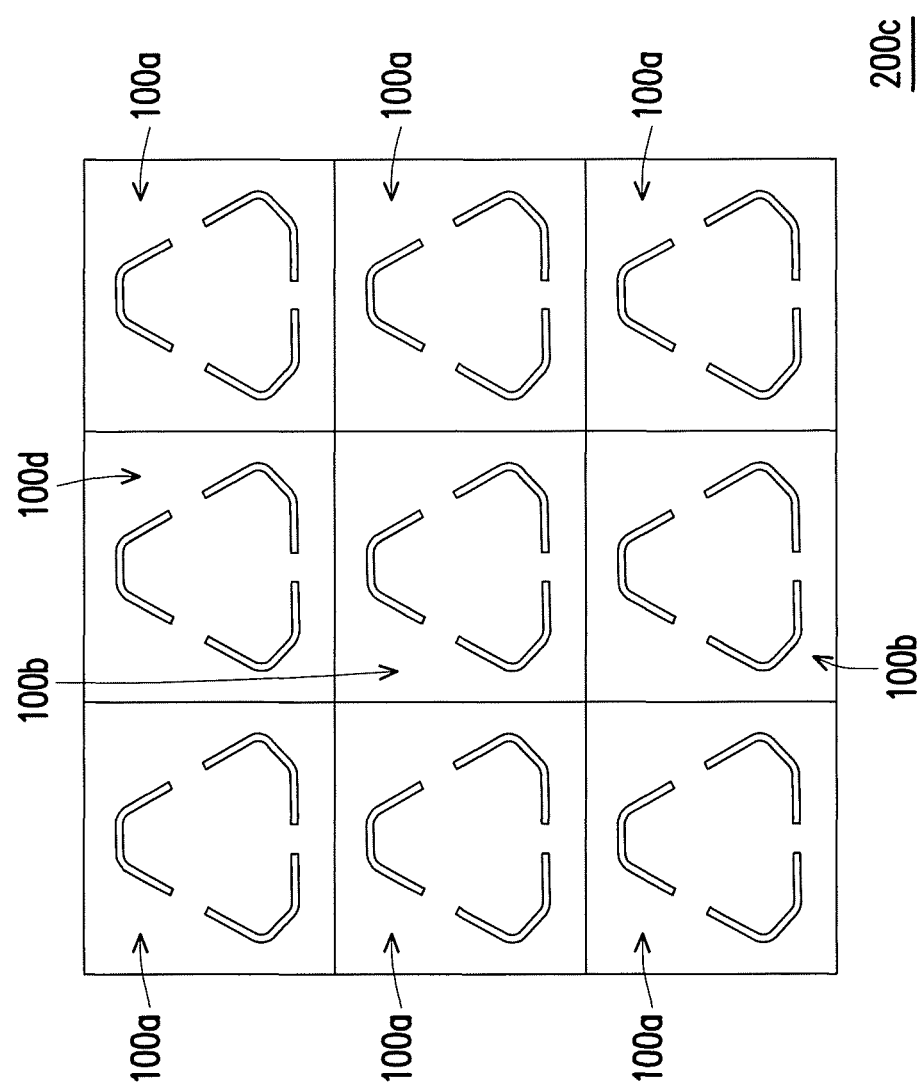
FIG. 8A is a schematic top view of an upper cover of a floor mat assembly of another embodiment of the disclosure.
Figure 8B:
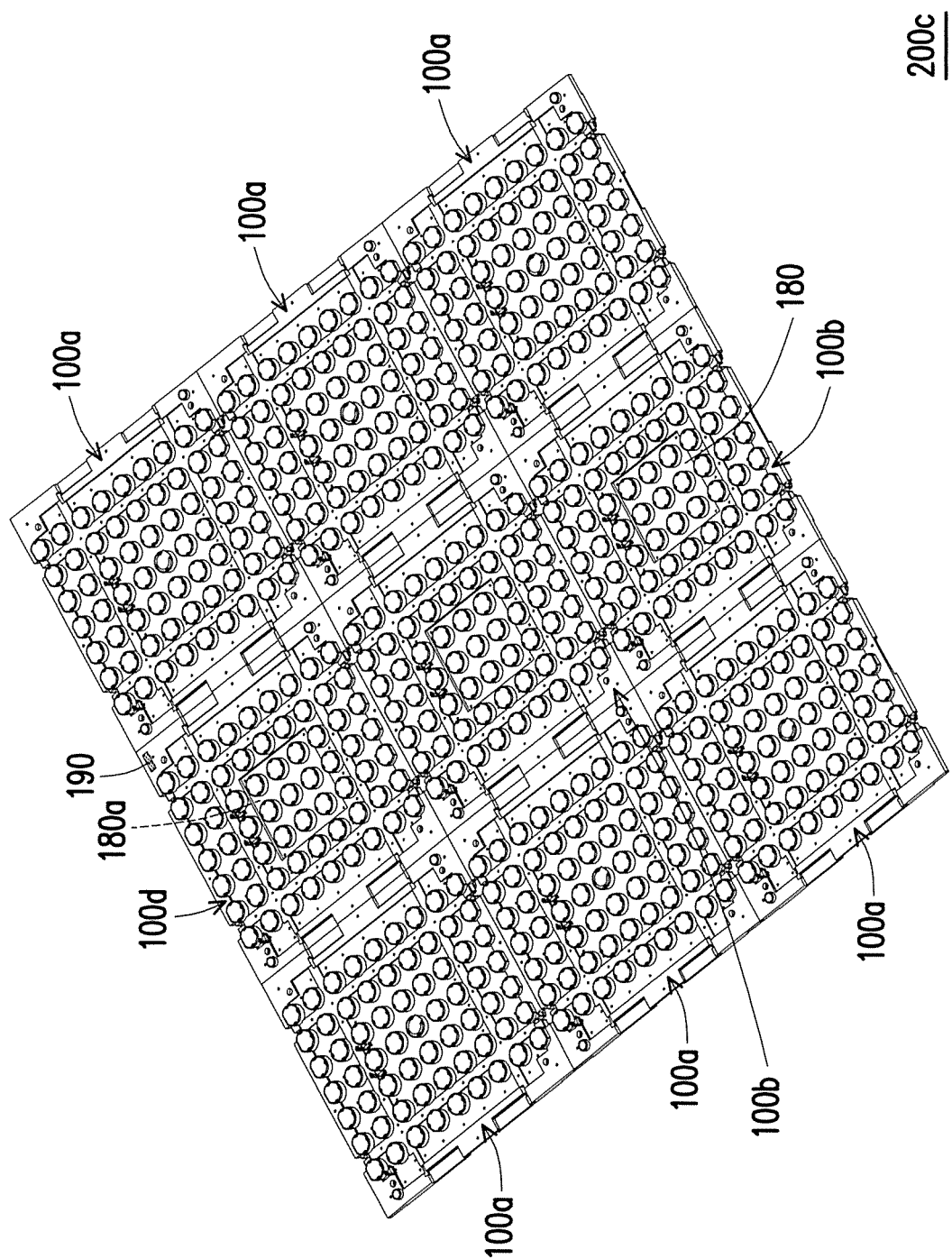
FIG. 8B is a schematic top view of a lower cover of the floor mat assembly of FIG. 8A.

FIG. 8A is a schematic top view of an upper cover of a floor mat assembly of another embodiment of the disclosure. FIG. 8B is a schematic top view of a lower cover of the floor mat assembly of FIG. 8A. For the convenience of description, parts of the components are omitted in FIG. 8A and FIG. 8B, and Please refer to FIG. 1B, FIG. 3 and FIG. 4 for detailed structures. In FIG. 8A and FIG. 8B, a floor mat assembly 200c includes six floor mat structures 100a, two floor mat structures 100b and one floor mat structure 100d, wherein the floor mat structure 100a, 100b and 100d are spliced together through the plurality of connecting components 202 (please refer to FIG. 7A or FIG. 7B) to form a shape of nine-square grid. Herein, the floor mat structure 100d having an antenna module 190 is located on the outside, which is beneficial for the reception and transmission of signals. Also, the floor mat structure 100b having a circuit board 180 is located between the two lines of the floor mat structure 100a, which is beneficial for the circuit configuration (the configuration of electric wires, the connector 160 and so on).

In short, the user can freely choose the number and types of the floor mat structures 100a, 100a', 100b, 100c, 100d, 100e and 100f and splice them together and decide the number and locations of the sensing elements 140a disposed thereon according to different requirements such as exercise trainings like TRX (Total Body Resistance Exercise), dancing game machine, or medical gait analysis and so on. Therefore, the floor mat structures 100a, 100a', 100b, 100c, 100d, 100e and 100f of the present embodiment can provide a buffering function and have the function of pressure sensing. In addition, the floor mat assembly 200a, 200b and 200c formed by the spliced floor mat structures 100a, 100c and 100d are more flexibility in use and the use efficiency may be increased at the same time.

In summary, in the design of a floor mat structure of the present invention, the sensing element is disposed on the bumps of the lower cover. When the user applies pressures to the floor mat structure to make the sensing element sense the pressure from the upper cover, the light bars disposed on the upper cover can illuminate to form an interaction relationship between the user and the floor mat structure. Moreover, the bumps of the lower cover can be used as a support to withstand the pressure imposed on the floor mat structure, thereby reducing the probability of damage to the floor mat structure. In addition, since the orthographic projections of the indicator blocks of the upper cover on the configuration surface of the lower cover does not overlap the bumps, the orthographic projections may be used to indicate the operators in following wire management works to avoid contacting the bumps. In short, the floor mat structure of the disclosure has multi-functions including the functions of protection and pressure sensing.

Although the disclosure has been disclosed in the above embodiments, the embodiments are not intended to limit the disclosure, and those skilled in the art may make some modifications and refinements without departing from the spirit and scope of the disclosure. Therefore, the scope of the disclosure is defined by the claims attached below.

What is claimed is:

1. A floor mat structure comprising:
   an upper cover comprising:
      a main body having an upper surface and a lower surface that are opposite to each other; and
      a plurality of indicator blocks separated from one another and disposed on the lower surface of the main body;
      a plurality of light bars disposed on the upper cover and embedded in the upper surface of the main body;
   a lower cover assembled to the upper cover comprising:
      a base having a configuration surface facing the lower surface; and
      a plurality of bumps separated from one another and disposed on the configuration surface of the base, wherein orthographic projections of the indicator blocks on the configuration surface does not overlap the bumps; and
   at least one sensing element disposed on the lower cover and located at at least one of the bumps, wherein when the sensing element senses pressure from the upper cover, the light bars illuminate.

2. The floor mat structure according to claim 1, wherein the upper cover further includes a plurality of protruding portions located at the lower surface of the main body, and orthographic projections of the protruding portions on the configuration surface completely overlap the bumps.

3. The floor mat structure according to claim 2, wherein the main body of the upper cover, the indicator blocks and the protruding portions are integrally formed.

4. The floor mat structure according to claim 1, wherein the main body of the upper cover has a plurality of first locking portions, and the base of the lower cover has a plurality of second locking portions, and the first locking portions respectively lock up the second locking portions to make the upper cover assembled to the lower cover.

5. The floor mat structure according to claim 1, wherein the main body of the upper cover has a plurality of grooves, and the grooves are located at the upper surface, and the light bars are respectively located in the grooves.

6. The floor mat structure according to claim 1, wherein the light bars illuminate blue light, red light, green light or combinations thereof.

7. The floor mat structure according to claim 1, wherein the light bars are arranged as a triangle, and the light bars are in series, in parallel or in serial parallel with one another.

8. The floor mat structure according to claim 7, further comprising:
   an illuminating pattern disposed on the upper cover and embedded in the upper surface of the main body, wherein the light bars surround the illuminating pattern.

9. The floor mat structure according to claim 8, wherein the illuminating pattern comprises numbers, words, symbols or combinations thereof.

10. The floor mat structure according to claim 1, wherein the bumps are arranged in an array on the configuration surface of the base, and the orthographic projections of the indicator blocks on the configuration surface are closed to the bumps.

11. The floor mat structure according to claim 1, wherein the shape of each of the bumps is cylindrical.

12. The floor mat structure according to claim 1, wherein the sensing element is a sensing film having a plurality of sensing points, and the sensing points are located at the pumps respectively.

13. The floor mat structure according to claim 1, further comprising:
   a plurality of buffers disposed on the lower cover and located at the bumps, wherein the buffers surround the sensing element to support the upper cover.

14. The floor mat structure according to claim 1, further comprising:
   at least one connector disposed on the lower cover and located at at least one side of the base, wherein the light bars and the sensing element are respectively electrically connected to the connector.

15. The floor mat structure according to claim 14, further comprising:
   a plurality of first electric wires electrically connected to the light bars and the connector; and
   at least one second electric wire electrically connected to the sensing element and the connector.

16. The floor mat structure according to claim 15, wherein the main body of the upper cover has a plurality of outlets penetrating through the upper surface and the lower surface, and one ends of the first electric wires extend through the outlets to connect to the light bars, and the other ends of the first electric wires are extended to be configured on the configuration surface of the base and are connected to the connector.

17. The floor mat structure according to claim 16, further comprising:
   a wire spring having a first end and a second end, wherein the first end is fixed to the base of the lower cover, and the first electric wires are extended through the second end.

18. The floor mat structure according to claim 14, wherein the base of the lower cover has a bottom surface with respect to the configuration surface and at least one storage groove, and the storage groove is disposed on the bottom surface, and the connector is stored in the storage groove.

19. The floor mat structure according to claim 18, further comprising:
   at least one encapsulation adhesive tape, wherein the connector is fixed in the storage groove with the encapsulation adhesive tape.

20. The floor mat structure according to claim 1, further comprising:
   a circuit board passing through parts of the bumps and disposed on the base of the lower cover, and the light bars and the sensing element are electrically connected to the circuit board respectively.

21. The floor mat structure according to claim 20, further comprising:
   a protection cover passing through parts of the bumps and covering the circuit board.

22. The floor mat structure according to claim 20, further comprising:
   an antenna module disposed on the lower cover and located at the base, wherein the antenna module is electrically connected to the circuit board.

23. The floor mat structure according to claim 1, further comprising:
   a plurality of fasteners, wherein each of the fasteners comprises a sleeve and a screw, and the sleeve passes through the lower cover and the upper cover, and the screw is threaded through the sleeve, so as to make the lower cover fixed to the upper cover through the fasteners.

24. A floor mat assembly comprising:
   a plurality of the floor mat structures according to claim 1, wherein the floor mat structures comprises at least one first floor mat structure and at least one second floor mat structure, and the second floor mat structure further comprises a first circuit board, and the light bars and the sensing element of the second floor mat structure and the light bars and the sensing element of the first floor mat structure are electrically connected to the first circuit board; and at least one connecting component, and the first floor mat structure is spliced together with the second floor mat structure through the connecting component.

25. The floor mat assembly according to claim 24, wherein the floor mat structures further comprises a third floor mat structure spliced together with the first floor mat structure and the second floor mat structure through the connecting component, and the third floor mat structure further comprises a second circuit board and an antenna module electrically connected to the second circuit board, and the light bars and the sensing element of the third floor mat structure are electrically connected to the second circuit board, and the second circuit board is electrically connected to the first circuit board.

* * * * *